United States Patent [19]

Kay et al.

[11] 4,146,365
[45] Mar. 27, 1979

[54] AFFINITY DETECTION APPARATUS

[75] Inventors: John W. D. Kay, Silver Spring; Leslie H. Kirkegaard, Ijamsville, both of Md.

[73] Assignee: Litton Bionetics, Inc., Kensington, Md.

[21] Appl. No.: 849,154

[22] Filed: Nov. 7, 1977

[51] Int. Cl.² .................................. G01N 33/16
[52] U.S. Cl. .................................. 422/57; 23/230 B; 195/139; 195/140; 424/12; 422/58; 422/104
[58] Field of Search ................ 23/230 B, 259; 424/12

[56] References Cited

U.S. PATENT DOCUMENTS

| 3,791,930 | 2/1974 | Saxholm | 23/230 B X |
| 3,843,450 | 10/1974 | Saxholm | 23/230 B X |
| 3,932,141 | 1/1976 | Beall | 23/259 |
| 3,970,518 | 7/1976 | Giaever | 23/230 B X |

*Primary Examiner*—Sidney Marantz
*Attorney, Agent, or Firm*—Robert A. Seldon

[57] ABSTRACT

In an affinity detection apparatus wherein the specific recognition of a first chemical for a second chemical is used to identify the presence of either, and being of the type normally including a receptical tray having at least one well sized to hold both an insertable member and a solution containing the first of said chemicals, and
an insertable member coated with the second chemical, the improvement comprising:
the coated member and well being complimentary shaped so as to define a first thin passageway between the member and well along substantially all the well periphery.

12 Claims, 2 Drawing Figures

AFFINITY DETECTION APPARATUS

BACKGROUND OF THE INVENTION

Field of the Invention

This invention broadly relates to affinity chromatography wherein the specific recognition of one chemical for a second is used to identify the presence of either. One such application is found in the immunoassay of immunochemicals such as antigens and antibodies. This invention is accordingly discussed in the content of immunoassay apparatus and, more particularly, in the context of apparatus including an immunochemically coated member and a receptical tray having a fluid-containing well sized to hold both a fluid sample and the coated member.

As used herein, the term "immunochemical" is generic to antigens and antibodies. For the purpose of this disclosure, a select immunochemical is defined as one whose presence or absence is to be determined, while an immobilized immunochemical is one which reacts with the select chemical to permit identification of the select chemical. Accordingly, when the select immunochemical is an antibody, the immobilized immunochemical will be an antigen specific thereto and, conversely, a select antigen will require the use of an immobilized antibody. For the sake of clarity, further discussion will be limited to a typical immunoassay process wherein the immobilized chemical is an antigen, the select chemical is an antibody and the fluid sample is one of human blood. It is to be understood, however, that other permutations and applications are within the scope of the invention.

Several direct and indirect methods for detecting the select immunochemical are known in the art. An example of a commonly practiced direct method employs competitive binding. A primary surface containing the immobilized immunochemical (typically an antibody to a hormone) is placed in a sample containing a known amount of labelled select immunochemical (typically, labelled hormone). Any (unlabelled) select immunochemical present in the sample competes with the labelled immunochemical for attachment to the immobilized immunochemical. Accordingly, a decrease in the latter from that obtained when a control sample containing only the labelled immunochemical is used, may be used to quantify the concentration of the former.

In the indirect method the coated member is coated with the immobilized immunochemical, such as the antigen of a particular virus, and immersed in the sample, where select antibodies, if any, become attached to the antigens. The member is removed, washed in an aqueous buffer solution, which is compatible with the antigen, to remove nonspecific reactions and placed in a second solution having a labelled reagent which recognizes the select immunochemical. The member is washed a second time to remove unbound labelled reagents and assayed.

Two labelling methods commonly used are radioisotopic means wherein the radioactively tagged reagent is detected by means of a counter, and enzyme-tagged means wherein the addition of a substrate to the tagged reagent produces a color change indicative of select immunochemical concentration. As will be apparent, the present invention is applicable to both direct and indirect methods as well as to both the radioisotopic and enzyme-tagged labelling methods.

Summary of the Prior Art

A receptical tray and an inserted member of the types conventionally used are illustrated in U.S. Pat. No. 3,932,141. The tray therein comprises a plurality of wells for receiving a fluid sample and a coated ball. The wells are arranged to receive samples of blood or serum which questionably contain the select immunochemical. The balls, in turn, are coated with a second immunochemical specific to the first. The wells are of sufficient depth and size to hold both a coated ball and a sample of the fluid.

One particularly troublesome characteristic associated with the apparatus according to the foregoing description, has been length and criticality of the required process time. It is highly desirable to reduce this process time both for economic reasons and, more importantly, for quickly diagnosing severely ill patients.

Such reductions have heretofore been provided by utilization of the "kinetic" measurements of the immunoassay system, rather than waiting until equilibrium has been achieved. In a kinetic system, concentrations of the select immunochemical are determined by the rate of reaction at specific times. Although concentrations may be more quickly determined in this manner by extrapolation, many variables such as temperature and agitation of the sample must be precisely controlled. By contrast, the method and apparatus of the equilibrium system are simpler.

The process time is predominantly limited by the diffusion time required for the immunochemicals in solution to reach the specific surface of the coated member. Thus, a second immunoassay device is shown in U.S. Pat. No. 4,018,886, wherein a plurality of finely divided magnetic particles, having a coated surface area, are dispersed in a vessel containing the fluid sample. The fluid is agitated so that the circulation of the particles throughout the fluid reduces the diffusion time normally required for antibodies in the fluid to reach the antigen-coated surfaces of the particles. The particles are then magnetically separated from the fluid. It is desirable to provide a less complex, and less costly test device.

SUMMARY OF THE INVENTION

In the immunoassay apparatus disclosed herein, the coated member and well have complimentary shapes so as to define a thin passageway between the member and well along substantially all the well periphery. The proximity of substantially all of the fluid sample to the coated member greatly reduces the diffusion time required. Preferred shapes disclosed herein additionally maximize the surface area available for the complexing interaction, thereby further minimizing process time. These and other features of the invention are more particularly shown in description of the preferred embodiment of which the following figures form a part.

DESCRIPTION OF THE PREFERRED EMBODIMENT

Figure 1:
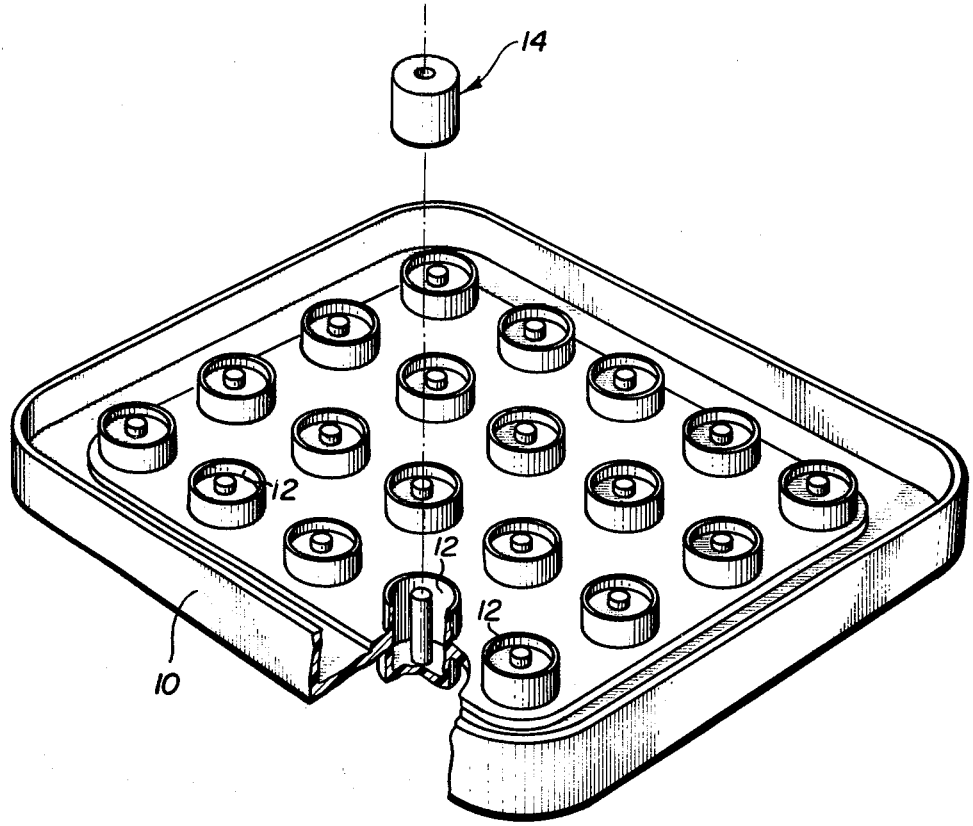
FIG. 1 is a perspective view of a receptical tray and a coated member constructed in accordance with the invention.

FIG. 1 is a perspective view of an immunoassay apparatus comprising a receptical tray and an insertable member constructed in accordance with the invention. The receptical tray 10 contains a plurality of fluid-containing wells 12 arranged to receive and hold a solution containing either a select immunochemical or an immuno-chemical specific thereto.

Typically, and for the purposes of the disclosure, the solution in the wells is a blood or serum sample wherein the presence or absence of a select antibody is to be determined. The well 12 is sized to additionally hold a carrier member 14 which is coated with an immobilized antigen, specific to the select antibody. As will be more clearly discussed below with reference to FIG. 2, the coated member 14 and the well 12 have complimentary shapes which decrease the time required for a sufficient quantity of antibodies to diffuse towards, and become attached to, the coated member 14.

Figure 2:
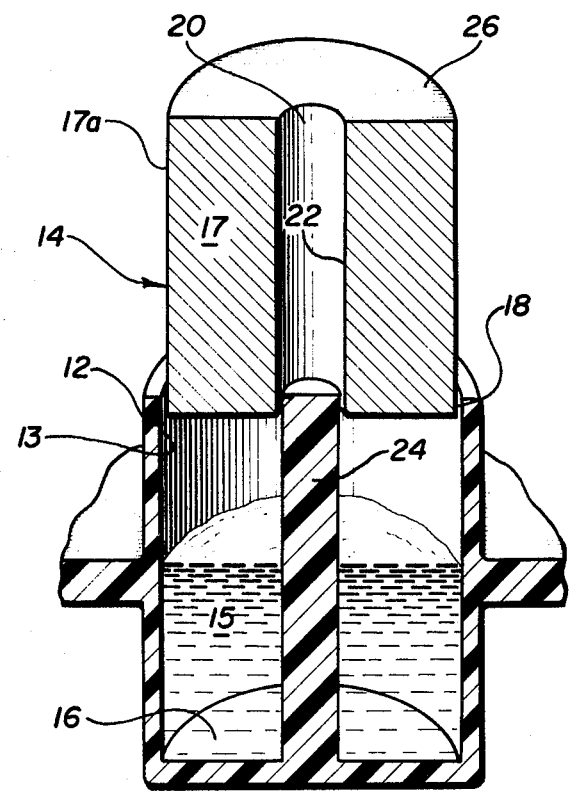
FIG. 2 is a sectional view of one well of the receptical tray of FIG. 1 and of the coated member oriented for insertion therein.

Turning to FIG. 2, there is shown a sectional view of the coated member 14 oriented for insertion into the well 12. The well 12 and member 14 are shown as generally cylindrical in shape, although it will be apparent that a wide variety of complimentary shapes may be utilized. The well 12 has an outer peripheral wall 13 and a base wall 16 which are formed from any material, such as polyethylene, which is non-toxic to the sample 15 and coated member 14. The coated member 14, in turn, includes a material 17 which is non-toxic to the sample and antigen, and an outer coating 17a of an antigen specific to the select antibody. Typically, the antigen coating is formed on a non-toxic material such as polystyrene. If the polystyrene is formed as a coating which is thereby interjacent to the material 17 and antigen, the choice for the material 17 is enlarged. The material 17 of the member 14 may conveniently be magnetically responsive for reasons set forth hereinbelow, and may, accordingly, comprise a ferrous interior and a rust-preventative coating formed from a material such as cadmium or nickel. The protective outer coating, such as polystyrene, is accordingly included to protect the antigen coating and sample 15 from any toxicity resulting from poisoning by the metals.

The coated member 14 is sized to fit within the well 12 in a manner which defines a passageway 18 therebetween. The passageway is preferably thin enough to minimize the path length of the antibodies diffusing from the more remote portions of the solution towards the antigen coating of the member 14, but sufficiently large to prevent a "blowout" of solution upon insertion of the member 14 into the well 12. A thin film of the sample is preferably formed interjacent the well and member. In the preferred embodiment, for example, the member 14 is in the order of 0.250 inches in height and 0.250 inches in diameter, while the passageway 18 is approximately 0.010 inches wide so that a thin film of the sample is formed interjacent the well and member.

To increase the antigen-coated surface area which intimately contacts the solution 15, to thereby maximize diffusion between the solution and carrier member, a longitudinal bore 20 may be formed in the member 14 to expose an inner peripheral surface 22. The well may be provided with a complimentary upwardly-extending protrusion 24 which fits within the bore 20 upon insertion of the member 14 therein. By this manner, a second thin film of solution may be formed between the outer periphery of the protrusion 24 and the inner periphery 22 of the member 14. The system described hereinabove is capable of reaching equilibrium in significantly shorter periods of time than in conventional designs and thereby yields greater reproducibility than the "rate" systems conventionally employed in the art to obtain results within these shorter periods of time.

As was briefly mentioned hereinabove, the member 14 may be conveniently provided with a magnetically responsive interior portion 17 which is formed, for example, from a ferric material. It thereby becomes possible to simultaneously insert and withdraw a plurality of such members 14 from a plurality of wells 12 by means of a magnetized cover member adapted to overlie the receptical tray 10 (FIG. 1). While magnetic manipulation of magnetically responsive carrier members is known in the art, the spherical members of the conventional assay devices contact the magnetic covers at only a point of tangency. Further, the magnetic field associated with the cover member is non-uniform over its surface area. Consequently, it has been difficult to prevent the spheres from "wandering" about the cover or dropping off during their transfer from sample to wash to reagent. Additionally, the inability to insure positional stability of the spheres has greatly limited the density of wells and, correspondingly, the number of assays per tray. Accordingly, an additional feature of the present invention is that it lends itself to more convenient magnetic manipulation of the coated members 14 and permits a greater well density, thereby further maximizing the cost-effectiveness of the assay. Accordingly, the top surface 26 of the member 14 is provided with a shape which is preferably complimentary to the magnetized portion of the cover member so that contact between the two occurs along a contact plane rather than a point. In the illustrated embodiment, the cylindrically shaped member 14 is provided with a substantially planar surface 26 so as to interface with a flat cover member along a contact plane, thereby establishing greater stability and control during the magnetic manipulation of insertable members.

An additional advantage associated with the shape of the presently disclosed insertable member 14 is that it lends itself to lettering. Consequently, different members having different antigen coatings may be simultaneously utilized in conjunction with a single receptical tray so that the blood sample may be simultaneously tested for a variety of antibodies.

Many variations and modifications which are obvious to one skilled in the art are possible. For example, the surface of the member 14 may be rough to provide more antigen-coated surface area and may, in the extreme case, be a mesh or screen. Additionally, the member 14 and wells 12 need not necessarily be round, as illustrated, but may also be triangular, square, etc., in cross section. Also, the protuberances 24 may extend from the cover, rather than the wells, to further restrict unwanted movement of the members 14. Further, transfer means associated with a cover member and engaging either the inner periphery 22 or outer periphery of the member 14 may be utilized. All such variations and modifications are within the purview of the present invention which is defined solely by the appended claims.

We claim:

1. In an affinity detection apparatus wherein the specific recognition of a first chemical for a second chemical is used to identify the presence of either, and wherein said apparatus includes a receptical tray having at least one well, said well sized to hold both an insertable member and a solution containing the first of said chemicals, and an insertable member coated with the second chemical, the improvement comprising:

the surface area of the coated member and the well wall being complimentary shaped so as to define a first thin passageway between the insertable member and the well along substantially all the well wall.

2. The apparatus of claim 1 wherein the insertable member includes a cavity communicating with at least one external surface thereof, the walls of the cavity being coated with the second chemical.

3. The apparatus of claim 2 wherein at least a portion of the well is defined between the outer periphery of an inner wall and the inner periphery of an outer wall so as to have a generally ring-shaped cross-section, and the member includes an interior, generally longitudinal bore in communication with at least one end face and sized to circumvent the inner wall of the well upon the insertion of the endface into the well, whereby a second fluid-accomodating passageway is defined between the outer periphery of the inner well wall and the bore wall.

4. The apparatus of claim 3 wherein the inner well wall is defined by the lateral periphery of a generally upwardly projecting protuberance extending from the bottom of the well.

5. The apparatus of claim 4 wherein the well has a generally annular cross-section in the direction transverse to the well depth, and the insertable member is a generally cylindrical shell of a thickness sized to freely fit within the annular well.

6. The apparatus of claim 4 wherein the insertable member includes an interior region of magnetically attractable material.

7. The apparatus of claim 6 further including a cover member adapted for placement on the receptical tray and having a magnetic region overlying the well during such placement for magnetically extracting the member therefrom and wherein the upwardly facing end of the inserted member is complimentary to the surface of the cover member overlying the well.

8. The apparatus of claim 6 wherein the insertable member includes a magnetically attracted core which is non-toxic to the solution and an immunochemical-attractive overcoating.

9. The apparatus of claim 8 wherein the overcoating is formed from polystyrene.

10. The apparatus of claim 8 wherein the magnetic core includes an interior magnetic portion and protective coating.

11. The apparatus of claim 10 wherein the core coating is formed from cadmium.

12. An affinity detection apparatus wherein the specific recognition of a first chemical for a second chemical is used to identify the presence of either, and wherein said apparatus includes a receptical tray having a matrix of wells sized to hold both an insertable member and a solution containing the first of said chemicals, the improvement comprising:

an insertable member coated with the second chemical, and having a bore, the insertable member and the well being complimentary shaped so as to orient the bore in a generally vertical direction in communication with the upper region of the well and to define a first thin passageway between the insertable member and well along substantially all the well wall; and a cover member adapted for placement on the receptical tray and having a matrix of protuberances spaced to overlie the wells during such placement and sized to fit with the bores of the insertable members to maintain the insertable members in alignment with the wells during simultaneous transfer of the members into and out of the tray.

* * * * *